US011980576B2

(12) United States Patent
Sledge et al.

(10) Patent No.: US 11,980,576 B2
(45) Date of Patent: May 14, 2024

(54) SURGICAL TRACTION SYSTEM

(71) Applicants: Scott Sledge, San Antonio, TX (US); Todd Hargroder, San Antonio, TX (US)

(72) Inventors: Scott Sledge, San Antonio, TX (US); Todd Hargroder, San Antonio, TX (US)

(*) Notice: Subject to any disclaimer, the term of this patent is extended or adjusted under 35 U.S.C. 154(b) by 0 days.

(21) Appl. No.: 17/354,563

(22) Filed: Jun. 22, 2021

(65) Prior Publication Data
US 2022/0401281 A1   Dec. 22, 2022

(51) Int. Cl.
| | |
|---|---|
| *A61G 13/00* | (2006.01) |
| *A61B 17/00* | (2006.01) |
| *A61B 17/02* | (2006.01) |
| *A61B 17/32* | (2006.01) |
| *A61F 5/04* | (2006.01) |
| *A61F 5/048* | (2006.01) |
| *A61G 13/10* | (2006.01) |

(52) U.S. Cl.
CPC ........ *A61G 13/0036* (2013.01); *A61B 17/025* (2013.01); *A61B 17/320016* (2013.01); *A61F 5/04* (2013.01); *A61F 5/048* (2013.01); *A61G 13/101* (2013.01); *A61B 2017/00477* (2013.01); *A61B 2562/0261* (2013.01)

(58) Field of Classification Search
CPC .............. A61G 13/0036; A61G 13/101; A61G 7/1013; A61G 7/1019; A61G 7/1017; A61G 7/1044; A61G 7/05; A61B 17/025; A61B 17/320016; A61B 2017/00477; A61B 2562/0261; A61F 5/04; A61F 5/048; A61F 5/042; A61H 1/02; A61H 1/0218; A61H 1/0237; A61H 1/0222; A61H 1/0229

USPC ......... 602/32–36, 39; 5/600, 612, 621, 83.1, 5/85.1, 87.1, 84.1, 89.1
See application file for complete search history.

(56) References Cited

U.S. PATENT DOCUMENTS

| | | | | |
|---|---|---|---|---|
| 4,616,637 | A * | 10/1986 | Caspari | A61F 5/04 |
| | | | | D24/188 |
| 4,930,523 | A * | 6/1990 | Laico | A61F 5/3761 |
| | | | | 5/87.1 |
| 5,775,334 | A * | 7/1998 | Lamb | A61G 13/12 |
| | | | | 128/845 |
| 7,569,024 | B1 | 8/2009 | Reznik | |
| 7,857,779 | B2 * | 12/2010 | Gondringer | A61F 5/04 |
| | | | | 602/33 |

(Continued)

FOREIGN PATENT DOCUMENTS

CN   205434171 U * 8/2016

OTHER PUBLICATIONS

Mount Definition & Meaning—Merriam-Webster.pdf; www.merriam-webster.com; accessed Aug. 16, 2022 (Year: 2022).*

(Continued)

*Primary Examiner* — Caitlin A Carreiro
(74) *Attorney, Agent, or Firm* — John C. Cave; Gunn, Lee & Cave, PC

(57) ABSTRACT

The present invention discloses a surgical traction system with a hand gripped tension adjustment device that slidably mounts onto a boom structure. When activated the tension adjustment device moves down the boom structure and incrementally adjusts the tension in a traction rope. The boom structure attaches to a bracket assembly that mounts onto the short end of a surgical table.

8 Claims, 15 Drawing Sheets

(56) References Cited

U.S. PATENT DOCUMENTS

2009/0306568 A1\* 12/2009 Meyer ................. A61H 1/0218
602/33
2013/0074294 A1\* 3/2013 Lynch ................. A47G 21/167
24/535

OTHER PUBLICATIONS

Machine translation of CN-205434171-U (Year: 2016).\*
Smith & Nephew, A Simple Solution for Patient Positioning, handout, prior to Jun. 22, 2021, Smith & Nephew, Andover, MA.
Arthrex,Inc., Shoulder Positioning, handout, prior to Jun. 22, 2021, United States.

\* cited by examiner

SURGICAL TRACTION SYSTEM

CROSS-REFERENCES TO RELATED APPLICATIONS

Not Applicable

STATEMENT REGARDING FEDERALLY SPONSORED RESEARCH OR DEVELOPMENT

Not applicable.

BACKGROUND OF THE INVENTION

1. Field of the Invention

The present invention relates generally to the medical field, and more specifically to an apparatus and method for traction positioning for arthroscopic surgery and other joint distraction procedures.

2. Background of Related Art

Arthroscopy is an orthopaedic surgical procedure on joints in which examination and treatment is performed using an endoscope that is inserted through a small incision. Arthroscopy is frequently used for the knee, shoulder, elbow, wrist, ankle, foot, and hip.

Arthroscopy and other joint distraction procedures are commonly performed using a traction boom device. These devices typically use a rope and pulley system that connects to a surgery patient and pulls on and positions the patient in a manner that allows proper examination and treatment of the affected area of the body. Existing traction boom devices require weights or sandbags to position surgery patients, which have several limitations and issues. For example, using traction device weights necessitates spending time, space, and other resources locating and storing the weights. At times, nurses and other support staff must leave the operating room in the middle of a procedure to locate more weights. The weights can be heavy and must be lifted in order to connect them onto the traction boom device, thereby risking injury to nurses and support staff. The use of weights with traction boom devices also make it difficult to control and measure the amount of tension applied to the surgery patient.

Existing traction boom devices attach to the long side of operating tables, which creates other issues and limitations. For example, placement on the long side of the operating table requires removal and relocation of the traction boom device to the opposite side of the operating table during contralateral procedures. The traction boom device's location on the long side of the operating table can also interfere with safely moving patients between the operating table and the pre-operative or post-operative gurney, which requires removal of the device from the operating table prior to moving the patient onto and off the operating table.

The present invention improves these problems by using a hand gripped tension adjustment device that incrementally adjusts the tension in a traction rope, without the use of weights or sandbags, giving the operator better control over the amount of tension applied to the surgery patient. A tension gauge and display allow for precise measurements in the tension. The present invention also attaches to the end of the operating table thereby eliminating the need to detach the traction boom device during contralateral procedures and prior to moving the surgery patient onto and off the operating table.

SUMMARY OF THE INVENTION

The present invention discloses a surgical traction system for use in arthroscopic surgery or other joint distraction procedures. Unlike the prior art, the present invention does not require the use of weights and attaches to the short end of an operating table. The surgical traction system has a surgical table, bracket assembly, boom structure, tension adjustment device, and traction rope. The bracket assembly comprising of a base arm and two side arms mounts onto a short side wall of the surgical table. The boom structure comprising of a boom arm and support leg mounts onto the bracket assembly. A first guide member is connected to a first end of the boom arm and a second end of the boom arm is hingeably connected to a second guide member with a hinge pin. The second guide member is fixably connected to the support leg. The hinge pin allows the boom arm to rotate in a plane that is coplanar or parallel to the longitudinal axis of the support leg. The support leg comprises an upper member and lower member. A first gear assembly is positioned at the bottom end of the upper member of the support leg. Activation of the first gear assembly rotates the upper member of the support leg about its longitudinal axis and relative to the lower member of the support leg, which adjusts the position of the first end of the boom arm. A base housing mounts to the bottom end of the lower member of the support leg and a second gear assembly is housed within the base housing. Activation of the second gear assembly will vertically move the lower member of the support leg, which adjusts the height of the boom arm.

The tension adjustment device is comprised of a mounting member, first and second friction plates, springs, a tension adjustment lever, a release lever, a cam cleat, and a strain gauge system. The mounting member slidably mounts onto the upper member of the support leg of the boom structure thereby allowing the tension adjustment device to move up and down the support leg. The first friction plate is in frictional contact with the support leg. A camming surface is positioned at the upper end of the tension adjustment lever and bears against the first friction plate and a spring biases the first friction plate against the camming surface. When the tension adjustment lever is activated the camming surface rotates upward and pushes against the first friction plate causing the first friction plate to increase frictional contact with the support leg. The increase in frictional contact causes the first friction plate to grip the support leg and further rotation of the lever and camming surface causes incremental downward movement of the tension adjustment device on the support leg. The second spring of the tension adjustment device biases the second friction plate against the support leg creating frictional contact with the second friction plate and the support leg, which acts to prevent vertical movement of the tension adjustment device along the support leg when the tension adjustment lever is not activated. When the tension adjustment lever is activated, the frictional contact between the second friction plate and support leg is insufficient to prevent the tension adjustment device from moving vertically down the support leg because the force created by the frictional contact between the first friction plate and the support leg overcomes the force created by the frictional contact between the second friction plate and the support leg. Activation of the release lever reduces or eliminates the frictional contact between the second friction plate and the support leg allowing the tension adjustment device to unlock and move freely up and down the support leg when the tension adjustment lever is not activated.

The cam cleat mounts to the strain gauge system and is positioned to receive the traction rope. The strain gauge system is attached to the mounting member and consists of a strain gauge, readable display, controller, and power supply. The strain gauge measures the tension in the traction rope. The first guide member, the second guide member, and the cam cleat create a pathway for mounting and connecting the traction rope to the boom structure and tension adjustment device. One end of the traction rope can be attached to a surgery patient. The other end of the traction rope can be attached to the cam cleat. Activation of the tension adjustment lever of the first handle moves the tension adjustment device vertically down the longitudinal axis of the support leg in small increments thereby increasing tension in the traction rope. The increased tension adjusts the positioning of the surgery patient.

DETAILED DESCRIPTION OF THE INVENTION

Figure 1:
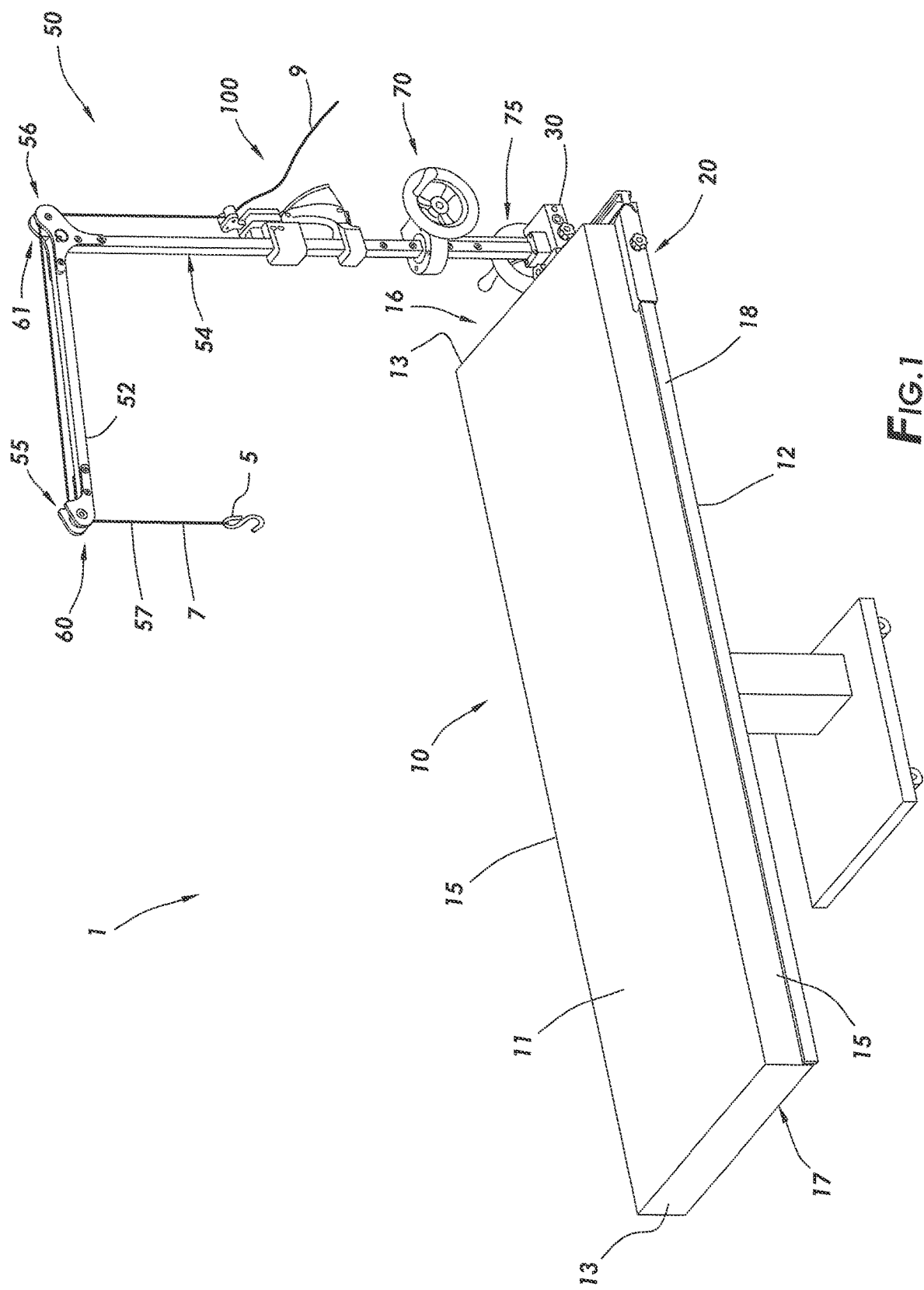
FIG. 1 is a perspective view of the surgical traction system of the present invention.
Figure 2:
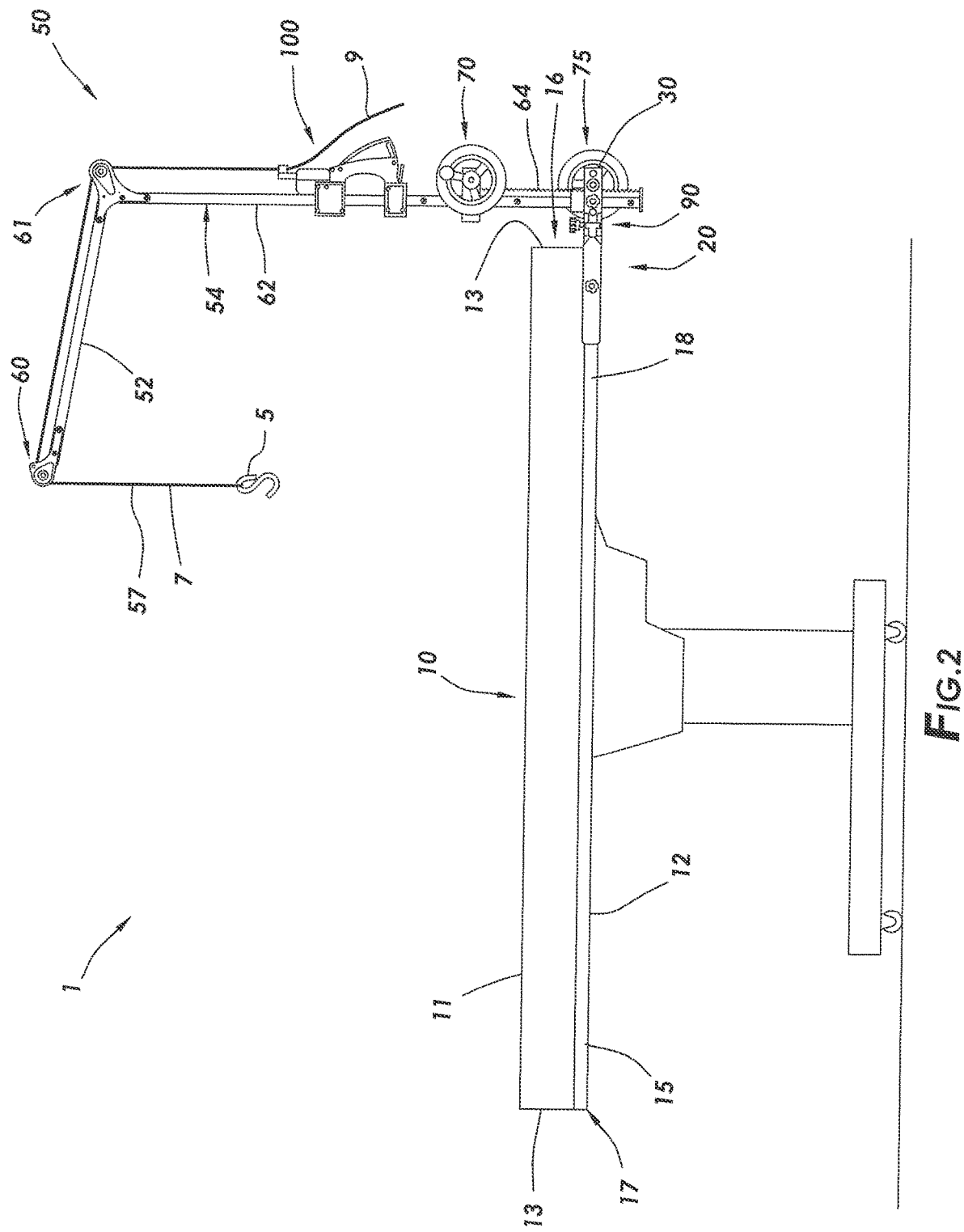
FIG. 2 is a side view of the surgical traction system.
Figure 3:
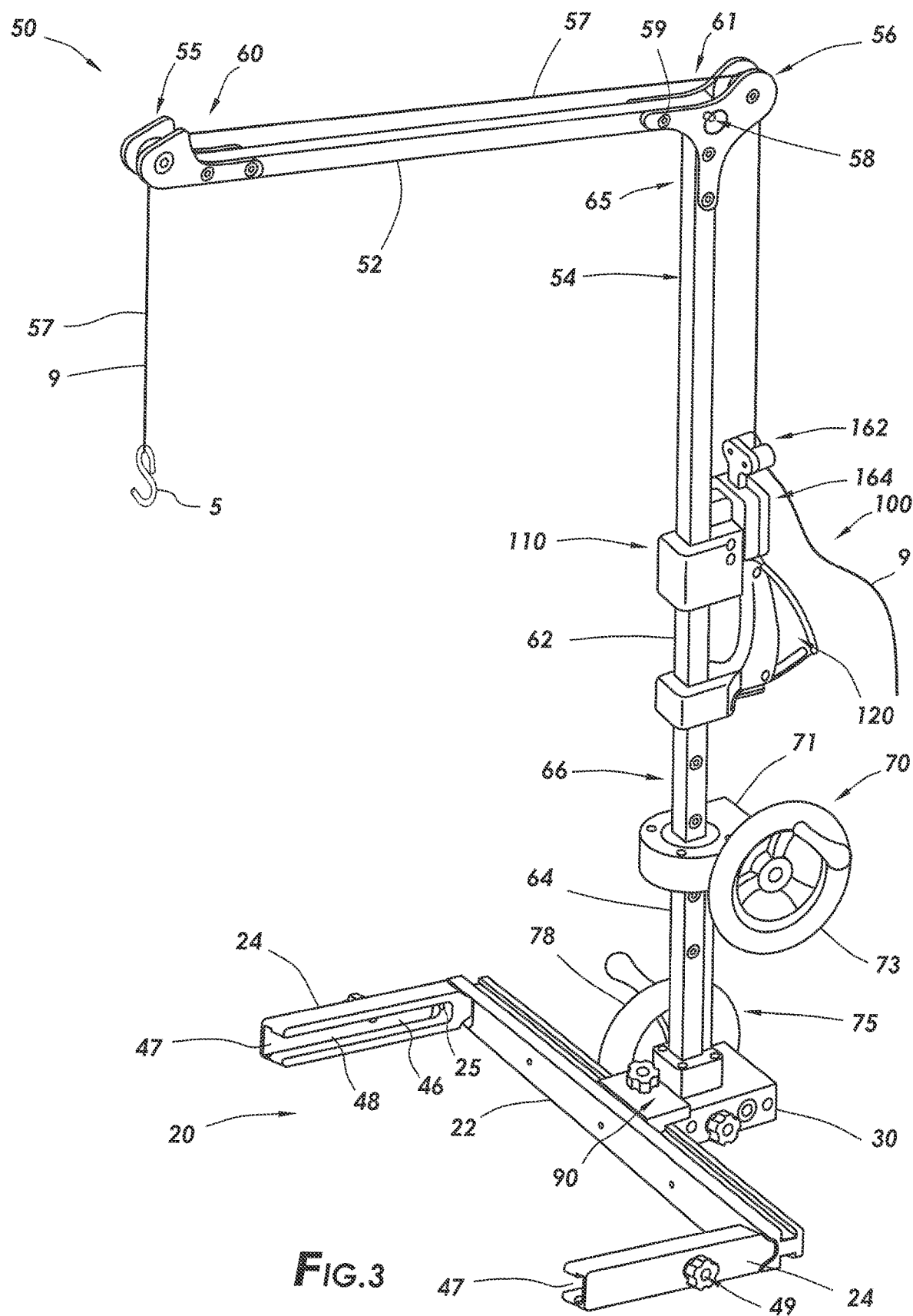
FIG. 3 is a perspective view of the surgical traction system without the surgical table.
Figure 4:
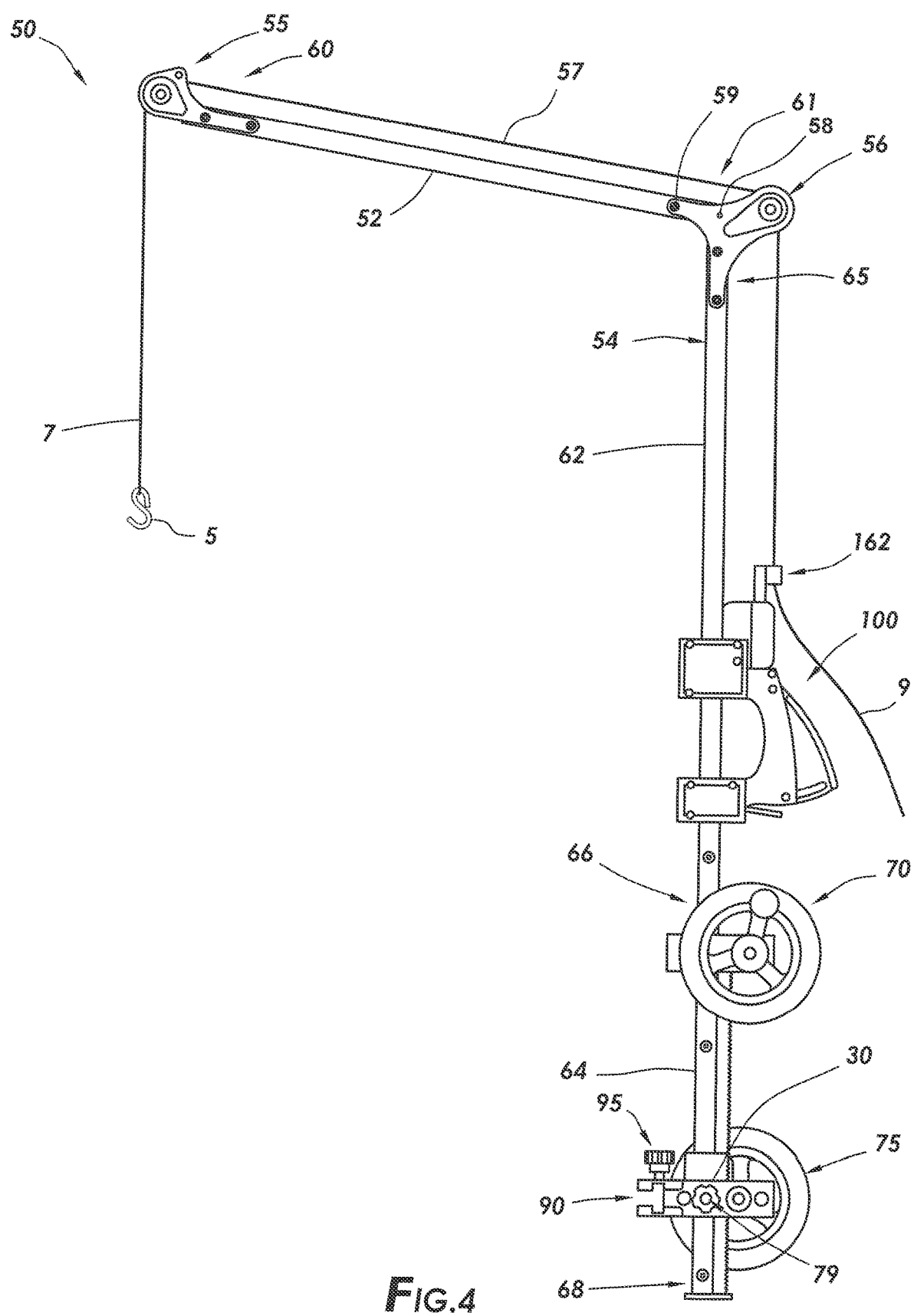
FIG. 4 is a side view of the boom structure and tension adjustment device of the surgical traction system with the boom arm in the locked position.
Figure 5:
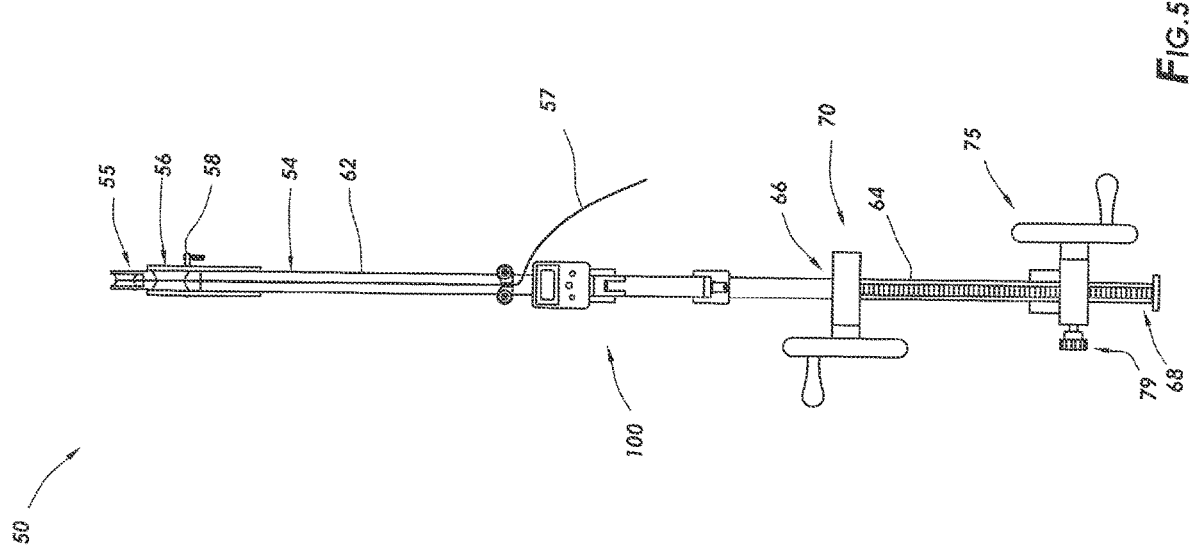
FIG. 5 is a front view of the boom structure and tension adjustment device of the surgical traction system.
Figure 6:
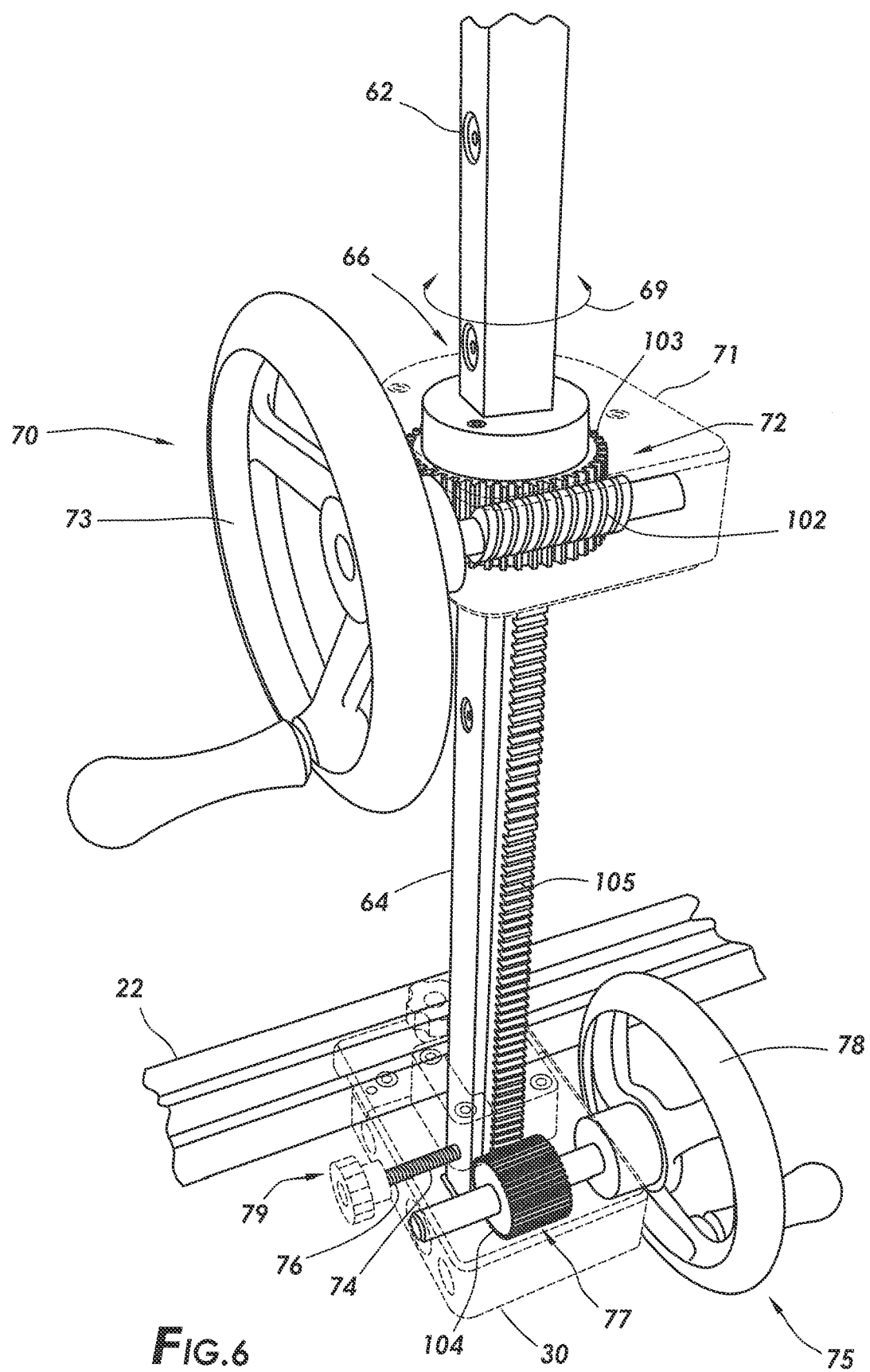
FIG. 6 is a perspective view of the upper gear system and lower gear system of the boom structure.
Figure 7:
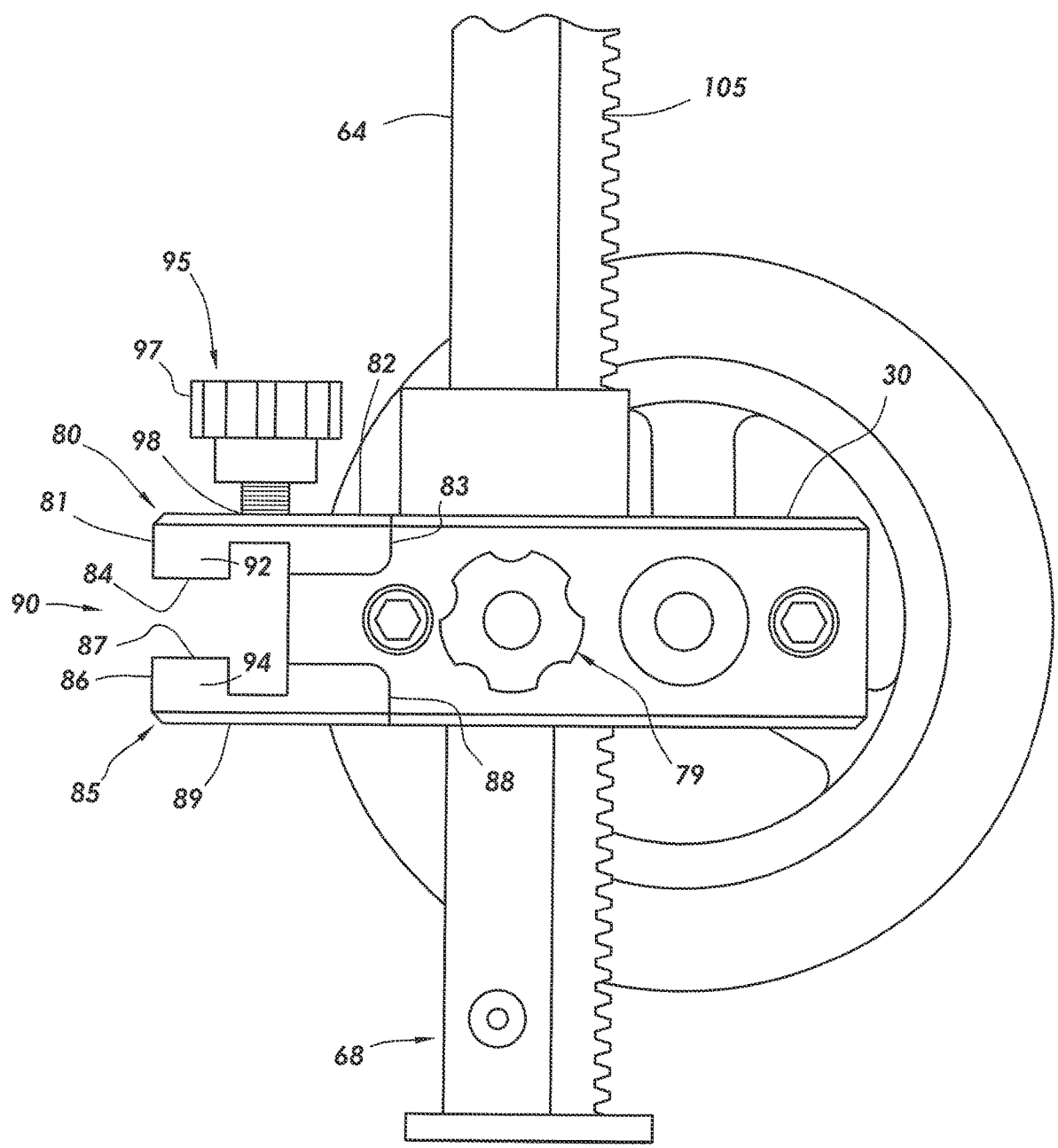
FIG. 7 is an enlarged side view of the base housing and boom structure mount.
Figure 8:
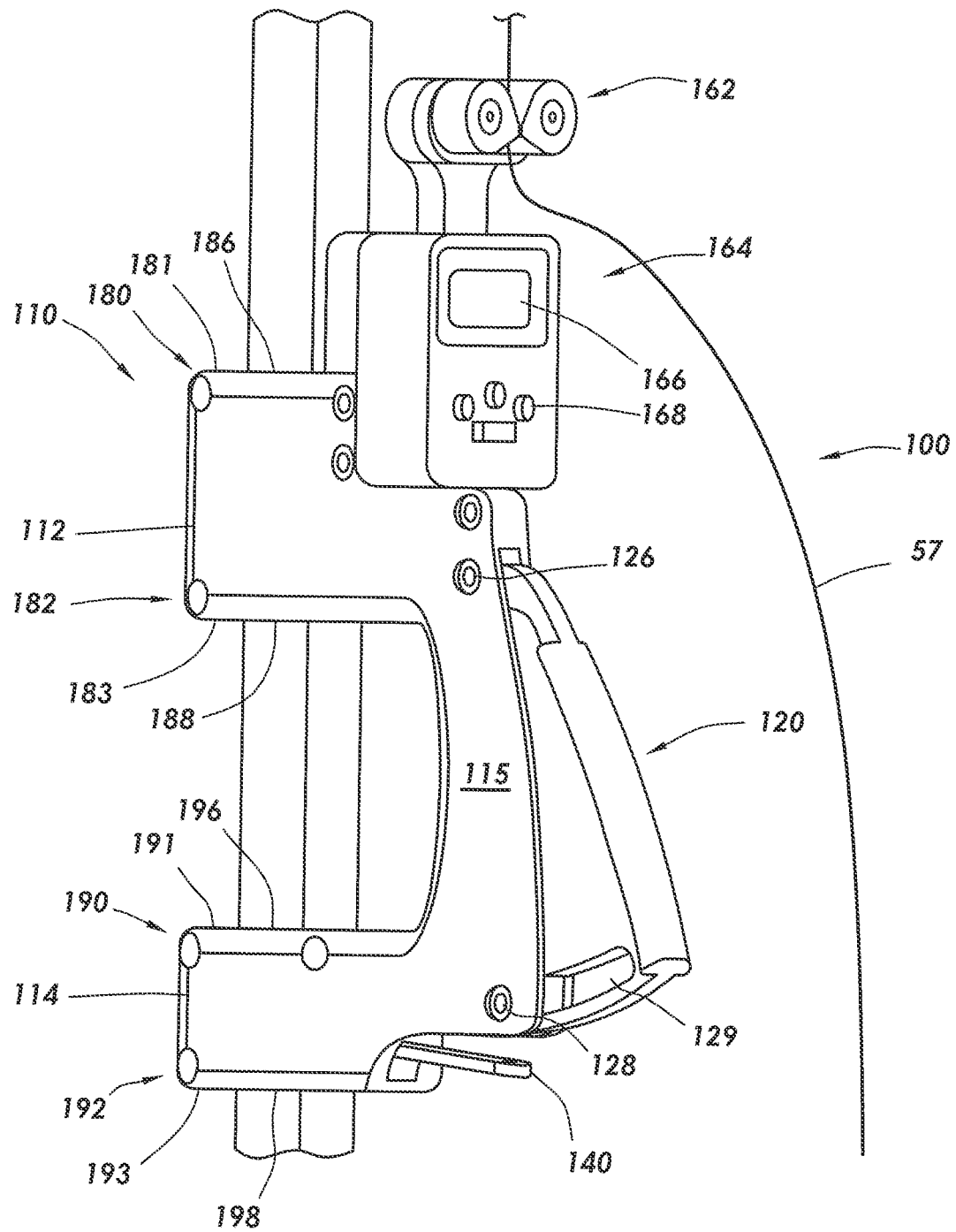
FIG. 8 is a perspective view of the tension adjustment device mounted onto the support leg of the boom structure.
Figure 9:
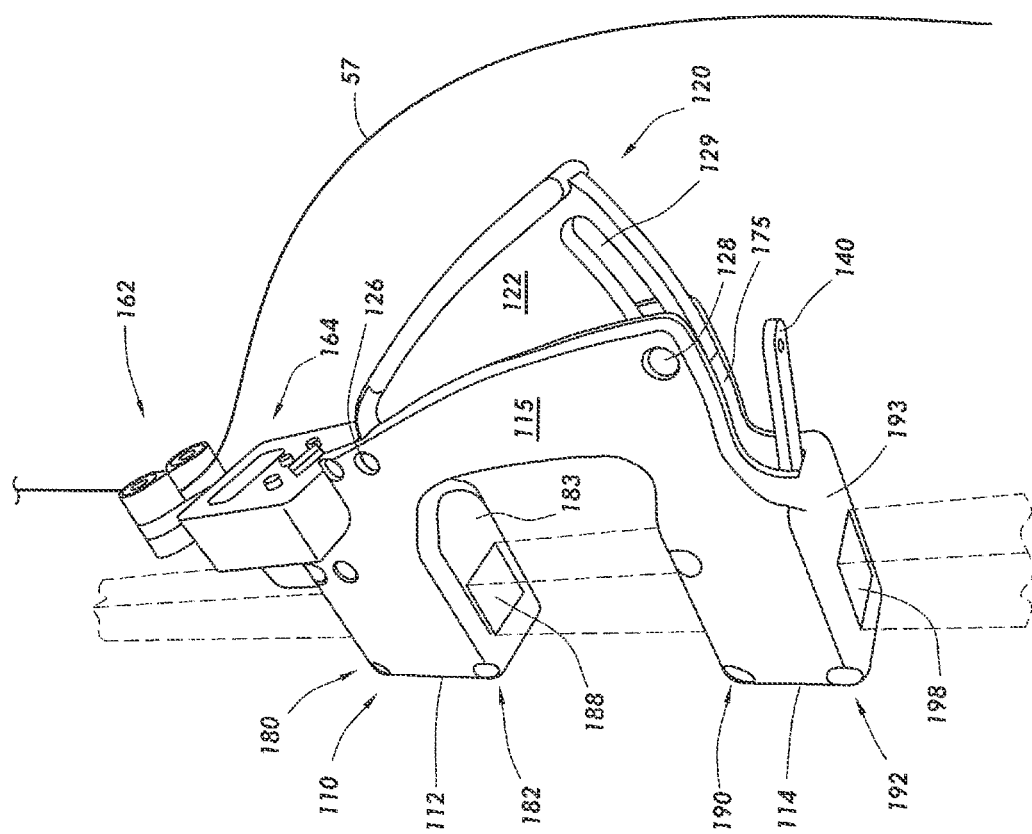
FIG. 9 is a bottom perspective view of the tension adjustment device.
Figure 10:
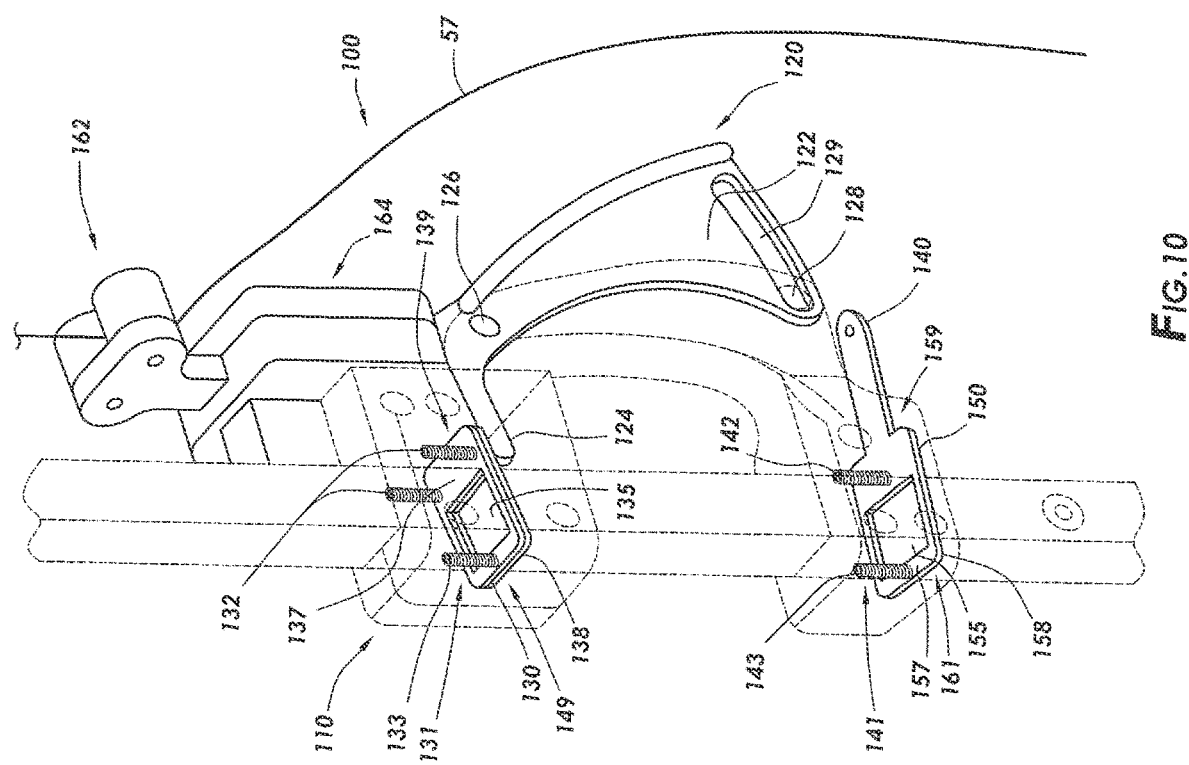
FIG. 10 is a top perspective view of the tension adjustment device.

As seen in FIGS. 1 and 2, the surgical traction system 1 comprises a surgical table 10, bracket assembly 20, boom structure 50, tension adjustment device 100, and traction rope 57.

The surgical table 10 comprises a rectangular top surface 11 and bottom surface 12, two short side walls 13 and two long side walls 15 extending between the top surface 11 and bottom surface 12, and a top end 16 and bottom end 17. In the preferred embodiment, the surgical table 10 is a standard operating table that is rectangular in shape with the short and long side walls 13, 15 positioned perpendicular to the top surface 11, but other shapes and arrangements are envisioned. The top surface 11 of the surgical table 10 is positioned to receive a surgery patient (not shown). A side rail 18 extends from the long side walls 15 of the surgical table 10.

As seen in FIGS. 1-3 and 14-18, the bracket assembly 20 comprises a base arm 22 and two side arms 24. The base arm 22 is an elongated member with a length approximately the width of the surgical table including the side rails and has an interior surface 31, a top surface 32, an exterior surface 33, a bottom surface 34, a first end 35, and a second end 36. The top surface 32 of the base arm 22 forms a channel 37 that runs from the first end 35 to the second end 36. The bottom surface 34 of the base arm 22 forms a channel 38 that also runs from the first end 35 to the second end 36.

The interior surface 31 is generally flat along its length with recesses 26 positioned at each end 35, 36. The exterior surface 33 is generally flat along its entire length. Two slots 21 are positioned in the exterior surface 33 at each end 35, 36 of the base arm 24 and each slot 21 extends from the interior surface 31 to the exterior surface 33. In the preferred embodiment, the exterior side surface 33 is smaller in height than the interior surface 31.

Each side arm 24 is an elongated member which slidably mounts to the base arm 22 and extends from the interior surface 31 of the base arm 22 at each end 35, 36. Each side arm 24 has an interior surface 40, a top surface 41, an exterior surface 42, a bottom surface 43, a first end 44, and a second end 45. A channel 48 in the interior surface 40 of each side arm 24 runs from the first end 44 to the second end 45. The second end 45 of each side arm 24 has an opening 47 to the channel 48. Opening 47 and the channel 48 of each side arm 24 are shaped to receive and correspond with the shape of the side rail 18 of the surgical table 10.

A protrusion 27 extends from the first end 44 of each side arm 24 which are shaped to correspond to and be received within the recesses 26 in the interior surface 31 of the base arm 22. The protrusions 27 of each of the side arms 24 is received into the corresponding recesses 26 such that the side arms 24 are generally positioned 90 degrees from the interior surface 31 of the base arm 22. This gives the bracket assembly 20 a generally rectangular U-shape to correspond with the shapes of the top or bottom ends 16, 17 of the surgical table 10.

The protrusions 27 are secured in the recesses 26 with a screw 25 which extends through the slot 21 of the base arm 22, through a threaded opening (not shown) in the protrusions 27 of each side arm 24, and into the channel 48 of each side arm 24. Preferably, the head of the screw 25 can be positioned within the slot 21 and a shoulder 8 positioned within the slot 21 can act as a stop and prevent the head of the screw 25 from passing through the slot 21. Each side arm 24 can be locked into a fixed position by tightening the head of the screw 25 against the shoulder 8 in the slot 21. The slot 21 is generally oval and is shaped and sized to receive the screw 25 such that the screw 25 can slidably move along the slot 21 when the head of the screw 25 is not tightened against the shoulder 8. The position of the side arm 24 may be adjusted by moving the screw 25 and side arm 24 along the slot 21, which adjusts the distance between the side arms 24. The distance between the side arms 24 can be adjusted to correspond to varying widths of the short side wall 13 of the surgical table 10.

The bracket assembly 20 mounts to the surgical table 10 by positioning the side rails 18 of the surgical table 10 in the channel 48 of each side arm 24. The bracket assembly 20 is secured to the surgical table 10 by adjusting the bracket locking members 49. In the preferred embodiment, each bracket locking member 49 comprises a screw 28 which screws into and through a threaded hole 29 in each side arm 24 such that the distal end of the screw 28 tightens against the side rails 18 of the surgical table 10 when the side rails 18 are positioned within the channel 48 of each side arm 24. In the preferred embodiment, the bracket assembly 20 is shaped to fit with a standard rectangular surgical table but other shapes are envisioned.

As seen in FIGS. 1-5, the boom structure 50 comprises a boom arm 52 and a support leg 54. The boom arm 52 is preferably a straight, elongated member and has a first end 60 and a second end 61. A first guide member 55 is connected to the first end 60 of the boom arm 52 and is positioned and shaped to receive the traction rope 57. In the preferred embodiment, the first guide member 55 is a pulley. The second end 61 of the boom arm 52 is rotatably connected to a second guide member 56 with a hinge pin 59. The second guide member 56 is fixably connected to the top end of the support leg 54. The hinge pin 59 allows the boom arm 52 to rotate in a plane that is coplanar or parallel to the longitudinal axis of the support leg 54. When the boom arm 52 extends to a desired angle from the support leg 54 a locking pin 58 can lock the boom arm 52 in that position in a manner well known in the art. Preferably, the desired angle is slightly greater than 90 degrees. When the locking pin 58 is released, the boom arm 52 can rotate into a resting position adjacent and generally parallel to the support leg 54. The boom arm 52 may be rotated to the resting position when the surgical traction system 1 is not in use.

The support leg 54 comprises an upper member 62 and a lower member 64. The second guide member 56 is connected to a top end 65 of the upper member 62 of the support leg 54. The second guide member 56 is shaped to receive the traction rope 57. In the preferred embodiment, the second guide member 56 is a pulley.

As seen in FIG. 1-6, a first gear assembly 70 is positioned at the bottom end 66 of the upper member 62 of the support leg 54 and comprises a first gear housing 71, a first gear system 72, and first gear handle 73. The first gear system 72 mounts to the bottom end 66 of the upper member 62 and is positioned within the first gear housing 71. The first gear handle 73 connects to and activates the first gear system 72. When the first gear handle 73 activates the first gear system 72, the upper member 62 of the support leg 54 rotates about its longitudinal axis relative to the lower member 64 of the support leg 54 as shown with rotational arrow 69. The rotation of the upper member 62 of the support leg 54 along its longitudinal axis allows for adjustment of the position of the first end 60 of the boom arm 52. In the preferred embodiment, the first gear system 72 is a worm gear wherein a screw gear 102 of the first gear system 72 extends from the first gear handle 73 and engages a wheel gear 103 connected to the upper member 62 of the support leg 54. Activation of the first gear handle 73 rotates the screw gear 102 which, in turn, rotates the wheel gear 103 and causes the upper member 62 of the support leg 54 to rotate about its longitudinal axis.

A base housing 30 mounts to the bottom end 68 of the lower member 64 of the support leg 54. A second gear assembly 75 consisting of a second gear system 77 and second gear handle 78 is housed within the base housing 30. The second gear handle 78 connects to and operates the second gear system 77. When the second gear handle 78 is rotated and activates the second gear system 77 of the second gear assembly 75, the lower member 64 of the support leg 54 moves vertically. The vertical movement of the lower member 64 of the support leg 54 adjusts the height of the support leg 54 which, in turn, adjusts the height of the boom arm 52. In the preferred embodiment, the second gear system 77 is a straight gear wherein a wheel gear 104 is connected to the second gear handle 78 and engages a rack gear 105 mounted on the lower member 64 of the support leg 54. Rotation of the second gear handle 78 rotates the wheel gear 104 causing vertical movement of the rack gear 105 and the lower member 64 of the support leg 54.

The vertical position of the lower member 64 of the support leg 54 can be locked into place by adjusting a second gear locking member 79. In the preferred embodiment, the second gear locking member 79 comprises a threaded member 74 which screws into and through a threaded hole 76 in the base housing 30 such that the distal end of the threaded member 74 tightens against the lower member 64 of the support leg 54 and holds it in place.

As seen in FIGS. 1-4, and 7, a boom structure mount 90 connects the base housing 30 to the bracket assembly 20. The boom structure mount 90 comprises an upper plate 80 and a lower plate 85. The upper plate 80 is generally rectangular in shape and has an interior surface 81, a top surface 82, an exterior surface 83, and a bottom surface 84. The bottom surface 84 of the upper plate 80 forms a shoulder 92. The lower plate 85 is generally rectangular in shape and has an interior surface 86, a top surface 87, an exterior surface 88, and a bottom surface 89. The top surface 87 of the lower plate 85 forms a shoulder 94 positioned opposite of shoulder 92. In the preferred embodiment, the exterior surface 83 and a portion of the bottom surface 84 of the upper plate 80 engages and attaches to the base housing 30 with screws (not shown). Likewise, the exterior surface 88 and a portion of the top surface 87 of the lower plate 85 engages and attaches to the base housing 30 with screws (not shown).

The upper plate 80 is positioned generally parallel to the lower plate 85. Shoulder 92 of the upper plate 80 is shaped and sized to correspond to and be received in the channel 37 in the top surface 32 of the base arm 22 of the bracket assembly 20. Likewise the shoulder 94 of the lower plate 85 is shaped and sized to correspond to and be received in the channel 38 of the base arm 22. The boom structure 50 mounts to the bracket assembly 20 by positioning the shoulders 92, 94 of the upper and lower plates 80, 85 of the boom structure mount 90 in the channels 37, 38 of the base arm 22 of the bracket assembly 20. In this manner, the shoulder 92, 94 can slide within the channels 37, 38 of the base arm and thereby adjust the position of boom structure 50.

The top surface 82 of the upper plate 80 contains a boom structure locking member 95. The boom structure 50 locks into place by adjusting the boom structure locking member 95. In the preferred embodiment, the boom structure locking member 95 comprises a threaded member 97 which screws into and through a threaded hole 98 in the top surface 82 of the upper plate 80 such that the distal end of the threaded member 97 tightens against the top surface 32 of the base arm 22 of the bracket assembly 20 when the boom structure 50 is mounted to the bracket assembly 20.

As seen in FIGS. 8-13, the tension adjustment device 100 comprises of a slide mounting member 110, a first friction plate 130, a first spring system 131, a tension adjustment lever 122, a second friction plate 150, a second spring system 141, a release lever 140, a cam cleat 162, and a strain gauge system 164. The slide mounting member 110 comprises an upper housing 112, a lower housing 114, and a handle support member 115 extending between the upper and lower housing members 112, 114. The upper and lower housing members 112, 114 are slidably mounted onto the upper member 62 of support leg 54 such that the slide mounting member 110 may move along the longitudinal axis of the support leg 54.

The upper housing 112 of the mounting member 110 forms an interior cavity 106 in which is housed the first friction plate 130 and the first spring system 131. A first opening 186 extends through an upper portion 180 of the upper housing 112 from the top surface 181 of the upper housing 112 to the cavity 106. A second opening 188 extends through a lower portion 182 of the upper housing 112 from the bottom surface 183 of the upper housing 112 to the cavity 106. The first and second openings 186, 188 are shaped and positioned to receive the upper member 62 of the support leg 54 there through with minimal clearance.

The first friction plate 130 has generally a flat rectangular shape and has a top surface 137, a bottom surface 138, a first end 139 positioned nearest the tension adjustment lever 122, a second end 149 positioned furthest from the tension adjustment lever 122, and an opening 135 extending through the first friction plate 130 from the top surface 137 to the bottom surface 138. In the preferred embodiment, the first friction plate 130 comprises of an upper plate 134 and a lower plate 136 that are both generally the same shape with the upper plate 134 secured parallel to the lower plate 136 so that they form one congruent plate. The opening 135 of the first friction plate 130 is shaped to correspond with the shape of the upper member 62 of the support leg 54 such that the support leg 54 is received therethrough with minimal clearance and the edges of the opening 135 of the first friction plate 130 can contact the upper member 62 of the support leg 54.

In the preferred embodiment, the first spring system 131 comprises a first spring 132, biased against the top surface 137 of the first end 139 of the first friction plate 130 and a second spring 133 biased against the top surface 137 of the second end 149 of the first friction plate 130. Each of the first and second springs 132, 133 extend from the cavity 106 into recesses 108 in the upper housing 112 to hold the springs in place. Each of the first and second springs 132, 133 of the first spring system 131 can be one or more springs.

Figure 11:
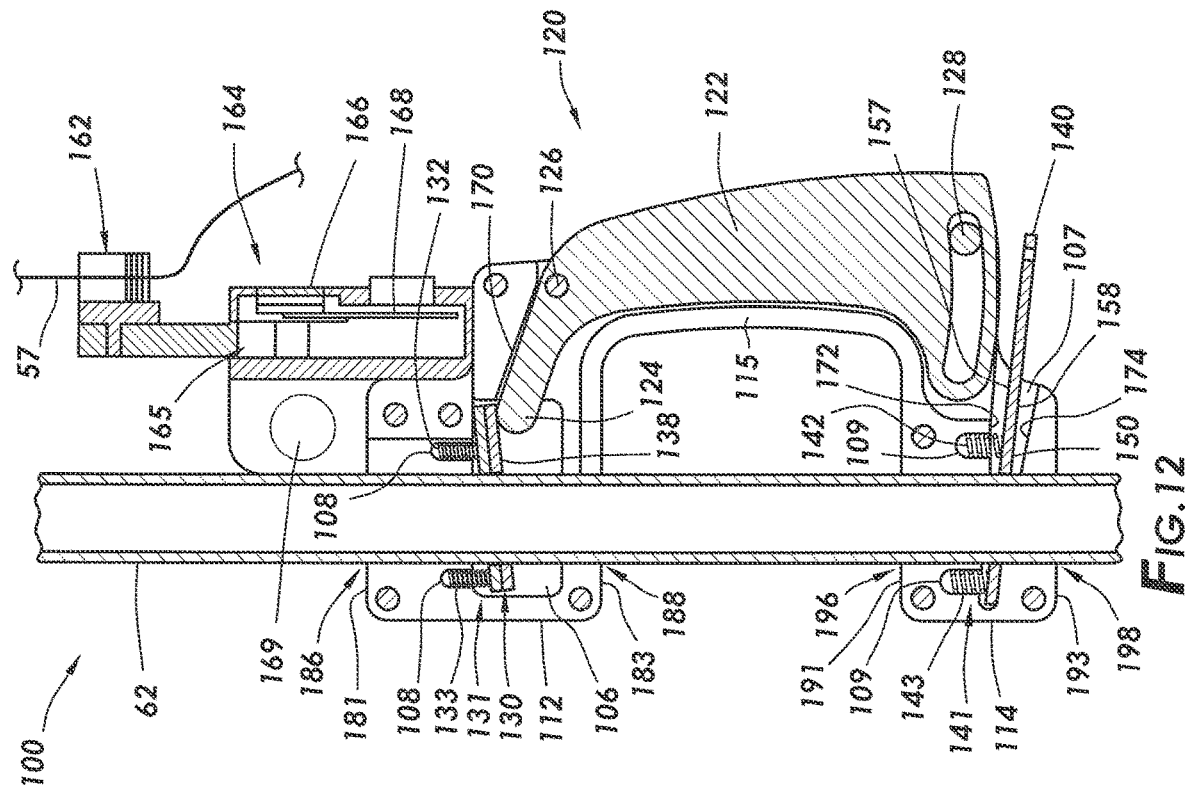
FIG. 11 is a sectional view of the tension adjustment device mounted onto the support leg of the boom structure.
Figure 12:
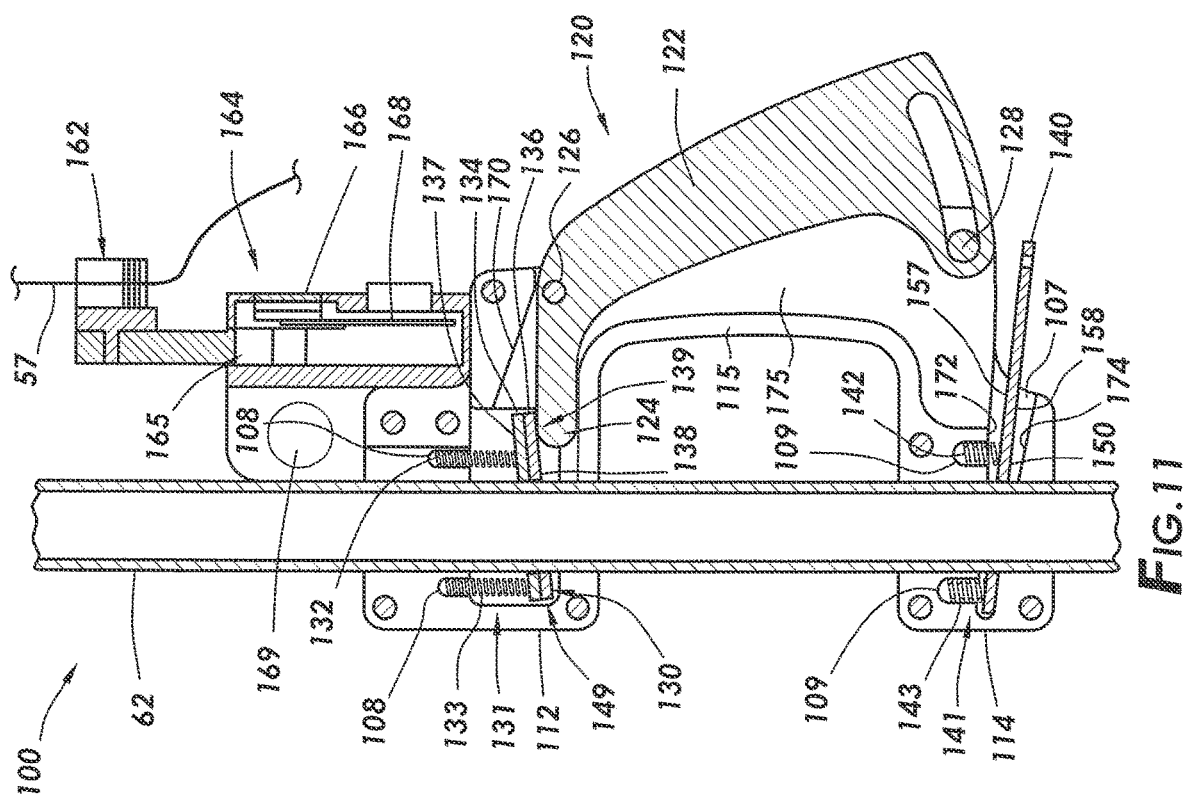
FIG. 12 is a sectional view of the tension adjustment device with the tension adjustment lever activated.
Figure 13:
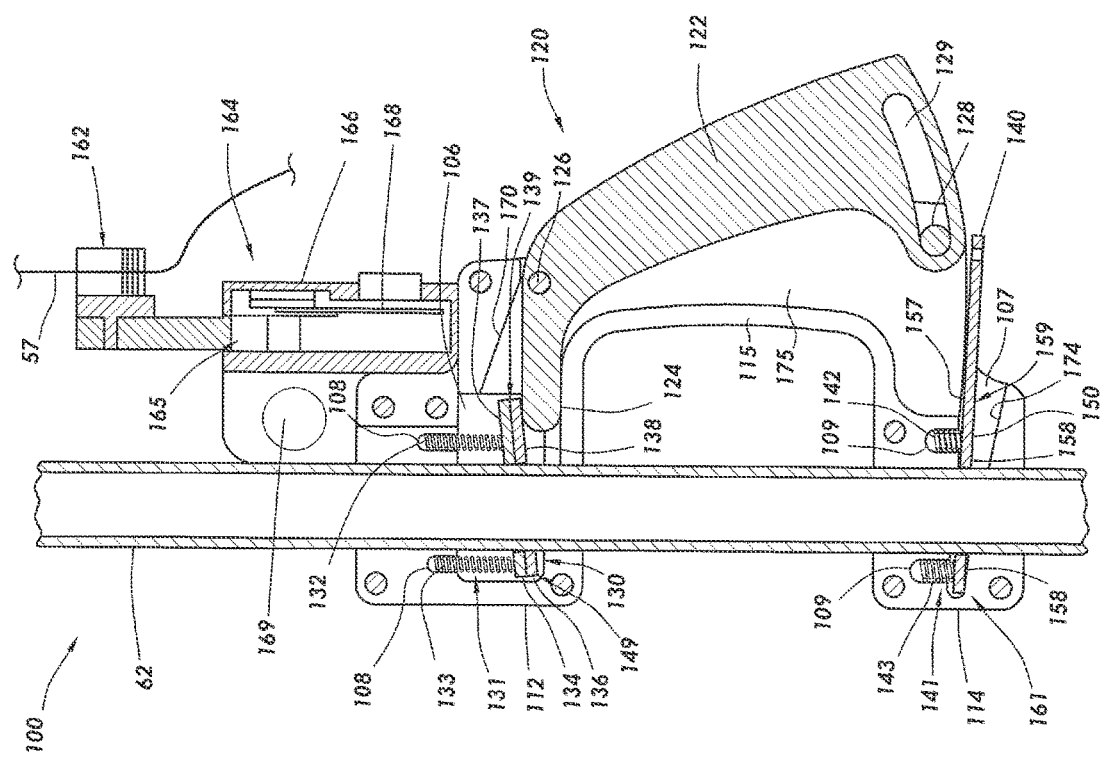
FIG. 13 is a sectional view of the tension adjustment device with the release lever activated.
Figure 14:
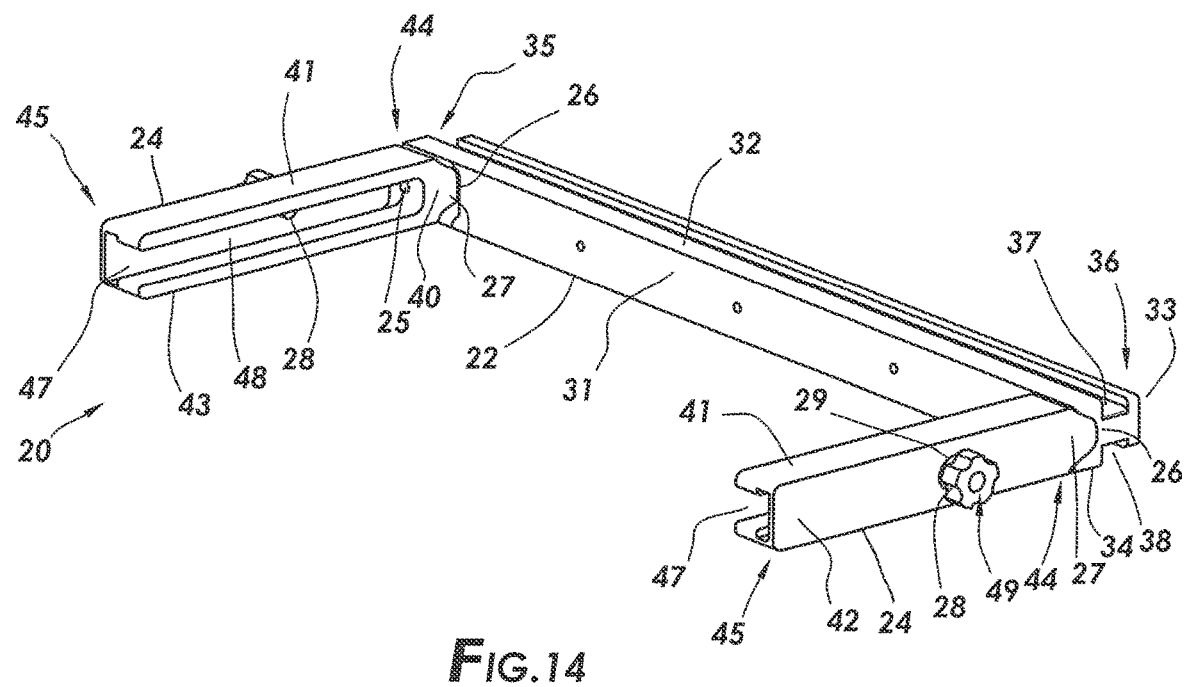
FIG. 14 is a perspective view of the bracket assembly system.
Figure 15:
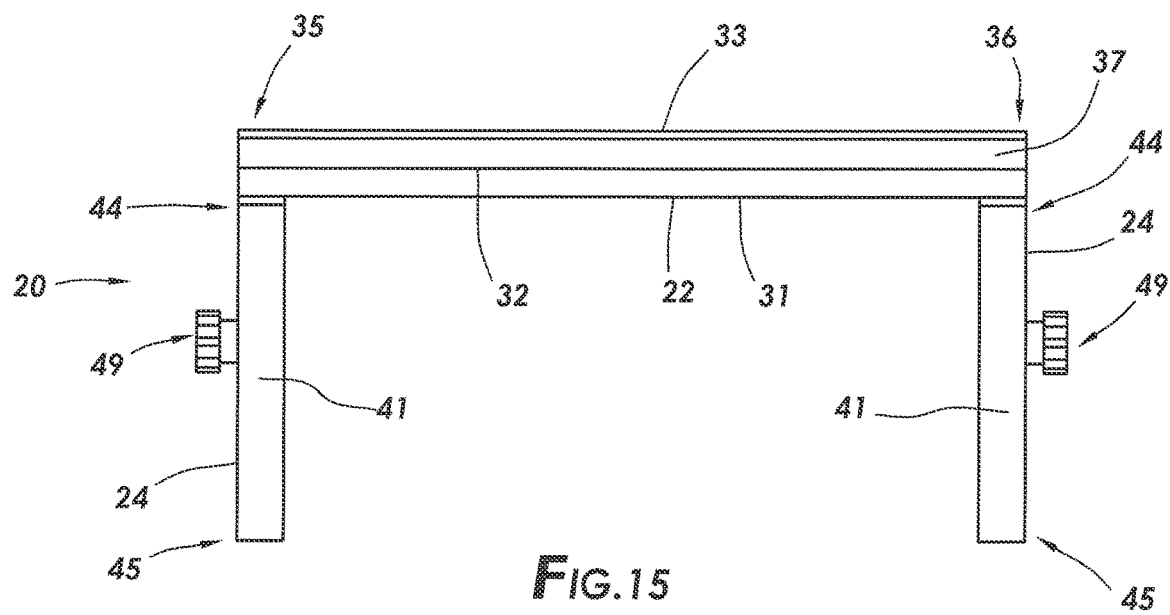
FIG. 15 is a top view of the bracket assembly system.
Figure 16:
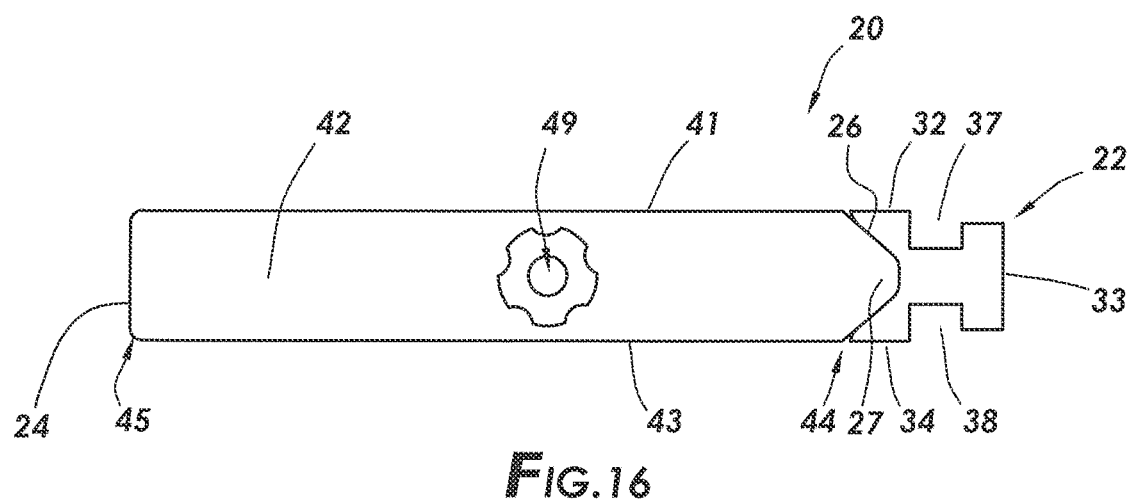
FIG. 16 is a side view of the bracket assembly system.
Figure 17:
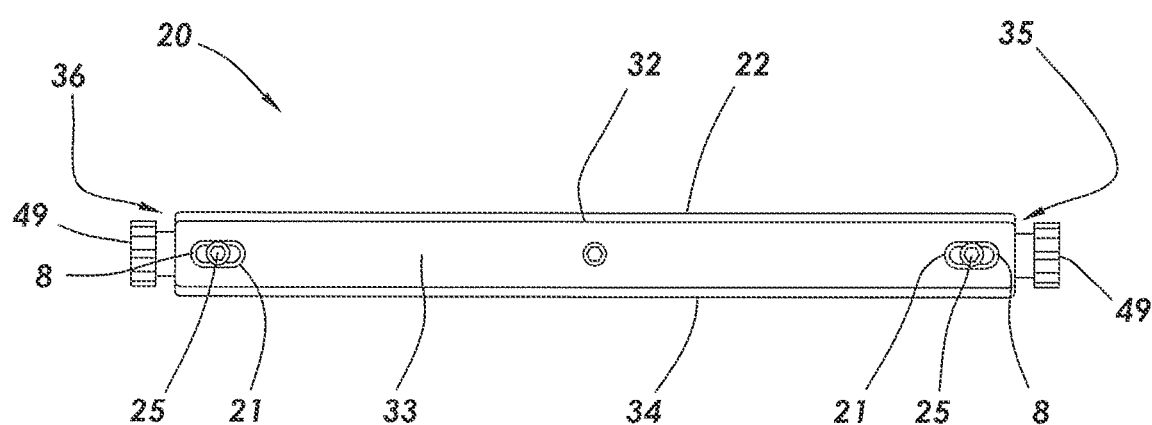
FIG. 17 is a back view of the bracket assembly system.
Figure 18:
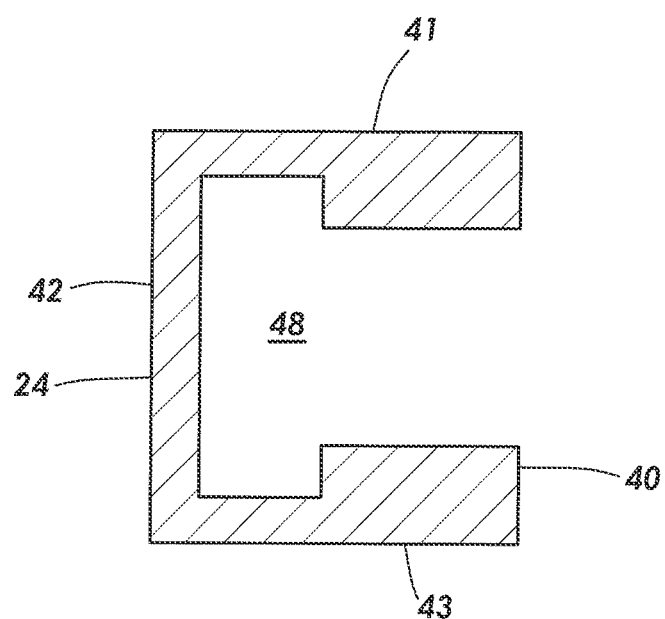
FIG. 18 is a cross-sectional view of the side arm of the bracket assembly system.

The tension adjustment lever 122 is an oblong member that is rotatably mounted to an upper end of the handle support member 115 with a hinge pin 126. The handle support member 115 forms a handle cavity 175 and both the shape of the handle support member 115 and the handle cavity 175 correspond to the shape of the tension adjustment lever 122. The tension adjustment lever 112 can rotate between a first position 200 as shown in FIG. 11 where it is fully extended from the handle cavity 175 and a second position 205 as shown in FIG. 12 where it is generally fully within the handle cavity 175. A shoulder 170 on the handle support member 115 positioned within the handle cavity 175 can act as a stop preventing further rotation of the tension adjustment lever 122 into the handle cavity 175.

A guide slot 129 is positioned at the lower end of the tension adjustment lever 122. A guide pin 128 is connected to the handle support member 115 and is positioned so that it extends through the guide slot 129. The guide slot 129 and the guide pin 128 act to guide the path of the tension adjustment lever as it rotates between the first and second positions 200, 205. The guide pin 128 can also act as a stop preventing further rotation of the tension adjustment lever 122 out of the handle cavity 175.

As seen in FIGS. 11 and 12, a camming surface 124 is positioned at the upper end of the tension adjustment lever 122 and bears against the bottom surface 138 of the first end 139 of the first friction plate 130. When the tension adjustment lever 122 is activated the lower end of the tension adjustment lever 122 is rotated towards the upper member 62 of the support leg 54 causing the camming surface 124 to rotate upwards and push against the bottom surface 138 of the first end 139 of the first friction plate 130. This, in turn, causes movement of the first end 139 of the first friction plate 130 in an upward direction and causes frictional contact between the edges of the opening 135 in the first friction plate 130 and the upper member 62 of the support leg 54. This frictional contact causes the first friction plate 130 to grip the upper member 62 of the support leg 54 such that further rotation of the tension adjustment lever 122 and camming surface 124 causes movement of the tension adjustment device 100 in a downward direction along the longitudinal axis of the upper member 62 of the support leg 54 where the first friction plate 130 remains in a fixed position on the support leg 54. This downward movement of the tension adjustment devices 100 compresses the first and second springs 132, 133 as shown in FIG. 12.

When the tension adjustment lever 122 is released the lower end of the tension adjustment lever 122 rotates away from the upper member 62 of the support leg 54 and the camming surface rotates downward to the released position as shown in FIG. 11. The biasing force on the top side 137 of the first friction plate 130 by the first spring system 131 causes the first friction plate 130 to also move in a downward direction.

Each time the tension adjustment lever 122 of the first handle 120 is activated the tension adjustment device 100 moves a short distance in a downward direction along the longitudinal axis of the upper member 62 of the support leg 54. This incremental movement of the tension adjustment device 100 allows for incremental adjustments to the position of the tension adjustment device 100 on the support leg 54 and for incremental adjustments to the tension in the traction rope 57.

As seen in FIGS. 9-13, the lower housing 114 of the mounting member 110 of the tension adjustment device 100 forms a cavity 107 which houses the second friction plate 150 and second spring system 141. A first opening 196 extends through an upper portion 190 of the lower housing 114 from the top surface 191 of the lower housing 114 to the cavity 107. A second opening 198 extends through a lower portion 192 of the lower housing 114 from the bottom surface 193 of the lower housing 114 to the cavity 107. The first and second openings 196, 198 are sized and positioned to receive therethrough the upper member 62 of the support leg 54 with minimal clearance. The second friction plate 150 has generally a flat rectangular shape and has a top surface 157, a bottom surface 158, a first end 159 positioned nearest the tension adjustment lever 122, a second end 161 positioned furthest from the tension adjustment lever 122, and an opening 155. The opening 155 of the second friction plate 150 is shaped to correspond with the shape of the upper member 62 of the support leg 54 such that the support leg 54 is received therethrough with minimal clearance and the edges of the opening 155 of the second friction plate 150 can contact the upper member 62 of the support leg 54.

In the preferred embodiment, the second spring system 141 comprises a first spring 142 biased against the top surface 157 of the first end 159 of the second friction plate 150 and a second spring 143 biased against the top surface 157 of the second end 161 of the second friction plate 150. Each of the top ends of the first and second springs 142, 143 of the second spring system 141 are positioned in recesses 109 in the upper portion 190 of the second housing 114 to hold the springs 142, 143 in place. Each of the first and second springs 142, 143 of the second spring system 141 can be one or more springs.

In the preferred embodiment, the bottom wall 174 of the cavity 107 is positioned at an angle allowing the second friction plate 150 to tilt within the cavity 107 with respect to the support leg 54. Preferably, the top wall 172 of the cavity 107 is also positioned at an angle causing the recess 109 receiving the first spring 142 to be positioned lower than the recess 109 receiving the second spring 143. The positioning of the recesses 109 and biasing force of the first and second springs 142, 143 of the second spring system 141 causes the second friction plate 150 to tilt within the cavity 107 such that the first end 159 of the second friction plate 150 is lower than the second end 161 of the second friction plate 150. The tilting of the second friction plate 150 causes the edges of the opening 155 in the second friction plate 150 to come into frictional contact with the support leg 54. In this manner, the second friction plate 150 grips the support leg 54 and prevents movement of the tension adjustment devise 100 when the tension adjustment lever 122 is not activated and is resting in its first position 200.

When the tension adjustment lever 122 of the first handle 120 is activated, the force created by the camming surface 124 against the first friction plate 130 is sufficient to overcome the frictional force created between the second friction plate 150 and the support leg 54. In this manner, the tension adjustment device 100 can move vertically down the longitudinal axis of the upper member 62 of the support leg 54.

A release lever 140 which is a generally flat and elongated member extends out of the cavity 107 from the first end 159 of the second friction plate 150. Activation of the release lever 140 (an upward movement) moves the first end 159 of the second friction plate 150 in an upward direction such that the second friction plate 150 pushes against and compresses the first and second springs 142, 143 of the second spring system 141. This, in turn, causes the second friction plate 150 to reduce frictional contact with the support leg 54. The reduction in frictional contact between the second friction plate 150 and the support leg 54 allows the tension adjustment device 100 to move freely along the longitudinal axis of the support leg 54.

As seen in FIGS. 8-13, the cam cleat 162 mounts to the strain gauge 164 of the tension adjustment device 100 and is positioned to receive the traction rope 57. However, it is anticipated that other traction rope securing mechanisms known in the art may be used. The cam cleat 162 secures the traction rope 57 to the tension adjustment device 100 such that the movement of the tension adjustment device 100 along the longitudinal axis of the upper member 62 of the support leg 54 adjusts the tension in the traction rope 57. Each time the first handle 120 of the tension adjustment device 100 is activated such that the tension adjustment device 100 moves in a downward direction along the longitudinal axis of the support leg 54, the tension in the tension rope 57 increases. When the release lever 140 of the tension adjustment device 100 is activated allowing the tension adjustment device 100 to move in an upward direction on the support leg 54, the tension in the tension rope 57 decreases.

The strain gauge system 164 of the tension adjustment device 100 mounts to the upper housing 112 of the slide mounting member 110 of the tension adjustment device 100. In the preferred embodiment, the strain gauge system 164 consists of a strain gauge 165, a readable display 166, a controller 168, and a power supply 169. The strain gauge system 164 is well known in the art and provides an easily readable display 166 showing the tension measured by the strain gauge 165. In the preferred embodiment, the readable display 166 is a digital display and the power supply 169 is a battery.

As seen in FIGS. 1-5, the traction rope 57 is mounted on the boom structure 50 and is long enough to and positioned to extend from the surgery patient (not shown) positioned on the surgical table 10 at the first end 7 through the first guide member 55 connected to the first end 60 the boom arm 52, through the second guide member 56 mounted on the support leg 54, and through the cam cleat 162. The second end 9 of the traction rope 57 is a free end and allows the rope to be pulled through the first and second guide members 55, 56 and the cam cleat 162. A hook 5 is attached to the traction rope 57 at the first end 7 of the traction rope 57 and is connected to the surgery patient (not pictured) positioned on the surgical table 10. When the tension rope 57 is mounted on the boom structure 50 and secured to the cam cleat 162 as described herein, movement of the tension adjustment device 100 in a downward direction along the longitudinal axis of the support leg 54 increases the tension in the traction rope 57. This in turn causes the hook 5 of the traction rope 57 to pull on the surgery patient (not pictured) at the point of connection to the hook 5.

Operation of the surgical traction system 1 can be described in the following manner:

The tension adjustment device 100 is mounted to the upper member 62 of the support leg 54 of the boom structure 50. The bracket assembly 20 is mounted to the surgical table 10 by positioning the side rails 18 of the surgical table in the channels 48 of each side arm 24 of the bracket assembly 20. The distance between each side arm 24 of the bracket assembly 20 is adjusted by sliding the screws 25 and the side arms 24 along the slots 21 of the base arm 22. The screws 25 of the bracket assembly 20 are tightened against the shoulder 8 positioned within the slot 21 to lock the side arms 24 into a fixed position on the base arm 22. The bracket locking member 49 of the bracket assembly 20 is tightened to lock the bracket assembly 20 onto the surgical table 10. The boom structure 50 is mounted to the bracket assembly 20 by mounting the boom structure mount 90 onto the base arm 22 of the bracket assembly 20. The boom structure locking member 95 of the boom structure mount 90 is tightened to secure the boom structure 50 onto the bracket assembly 20.

The boom arm 52 of the boom structure 50 is rotated into an extended position generally slightly greater than 90 degrees from the support leg 54 of the boom structure 50 and locked into that position with the locking pin 58. The traction rope 57 mounts to the boom structure 50 by positioning the traction rope 57 through the first and second guide members 55, 56 and securing the traction rope 57 in the cam cleat 162 of the tension adjustment device 100. The hook 5 located at the first end 7 of the traction rope 57 is hooked to the surgical patient (not pictured).

The position of the first end 60 of the boom arm 52 is adjusted by engaging the first gear handle 73 of the first gear system 70 such that the upper member 62 of the support leg 54 rotates around the longitudinal axis of the support leg 54. The height of the boom structure 50 is adjusted by engaging the second gear handle 78 of the second gear system 75 such that the support leg 54 moves along its longitudinal axis.

The tension adjustment lever 122 of the tension adjustment device 100 is activated to move the tension adjustment device 100 down the support leg 54 of the boom structure 50 in order to increase tension in the traction rope 57. Repeated activation of the tension adjustment lever 122 increases the tension in the tension rope 57 until the desired tension is achieved. The release lever 140 holds the tension adjustment device 100 in a fixed position on the support leg 54 and maintains tension in the traction rope 57 when the tension adjustment lever 122 is not activated. The strain gauge 165 measures the tension in the tension rope 57 and the tension is displayed in the strain gauge 165.

When the tension adjustment lever 122 is not activated, the release lever 140 can be activated to allow the tension adjustment devise 100 to freely move on the support leg 54 and release the tension in the traction rope 57.

Although the present invention has been described with reference to specific embodiments, this description is not meant to be construed in a limiting sense. Various modifications of the disclosed embodiments, as well as alternative embodiments of the invention will become apparent to persons skilled in the art upon the reference to the above-description of the invention. It is, therefore, contemplated that the appended claims will cover such modifications that fall within the scope of the invention.

We claim:

1. A surgical traction system comprising:
   a bracket assembly capable of mounting to a surgical table;
   a boom structure mounted to said bracket assembly said boom structure comprising a support leg and boom arm connected to said support leg wherein said support leg extends substantially in a vertical direction from said bracket assembly;
   a traction rope mounted on said boom structure;
   a tension adjustment device comprising a slide mounting member and a tension adjustment lever;
   wherein said tension adjustment device is attachable to said traction rope;
   wherein said slide mounting member is slidably mounted directly on said support leg;
   wherein said tension adjustment lever is connected to said slide mounting member; and
   wherein activation of said tension adjustment lever causes downward movement of said tension adjustment device along said support leg and increased tension in said traction rope.

2. The surgical traction system of claim 1 wherein:
   said bracket assembly has a generally rectangular U shape with a base arm and two side arms.

3. The surgical traction system of claim 2 wherein:
   said two side arms slidably mount to said base arm;
   a position of said side arms is capable of being adjusted to correspond with a width of an end of a surgical table; and
   said side arms are lockable on said base arm.

4. The surgical traction system of claim 1 wherein said tension adjustment device is lockable on said support leg.

5. The surgical traction system of claim 4 wherein said tension adjustment device further comprises:
   a release lever; and
   wherein activation of said release lever allows said tension adjustment device to slide freely on said support leg.

6. The surgical traction system of claim 1 wherein at least a first portion of said support leg is rotatable around a longitudinal axis of said support leg.

7. The surgical traction system of claim 1 wherein said support leg is moveable in a direction along its longitudinal axis.

8. The surgical traction system of claim 1 wherein:
   said boom arm is rotatably connected to said support leg; and
   said boom arm is lockable in a rotated position when said boom arm is extended at an angle from said support leg.

* * * * *